(12) United States Patent
Shibata et al.

(10) Patent No.: US 9,217,750 B2
(45) Date of Patent: Dec. 22, 2015

(54) SAMPLE PROCESSING APPARATUS AND CLEANING METHOD

(75) Inventors: Masaharu Shibata, Kobe (JP); Daigo Fukuma, Kobe (JP); Takaaki Nagai, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 628 days.

(21) Appl. No.: 12/609,282

(22) Filed: Oct. 30, 2009

(65) Prior Publication Data
US 2010/0108101 A1    May 6, 2010

(30) Foreign Application Priority Data

Oct. 30, 2008 (JP) .................... 2008-280578

(51) Int. Cl.
| | | |
|---|---|---|
| B08B 9/027 | (2006.01) | |
| G01N 33/00 | (2006.01) | |
| G01N 33/48 | (2006.01) | |
| G01N 21/00 | (2006.01) | |
| G01N 35/10 | (2006.01) | |
| B01L 3/02 | (2006.01) | |
| G01N 35/00 | (2006.01) | |
| G01N 35/04 | (2006.01) | |

(52) U.S. Cl.
CPC .......... *G01N 35/1004* (2013.01); *B01L 3/0293* (2013.01); *G01N 35/00712* (2013.01); *G01N 35/0095* (2013.01); *G01N 35/00594* (2013.01); *G01N 2035/0415* (2013.01); *G01N 2035/1032* (2013.01)

(58) Field of Classification Search
CPC ................... G01N 35/1004; G01N 35/00594; G01N 35/00712
See application file for complete search history.

(56) References Cited

U.S. PATENT DOCUMENTS

| | | | |
|---|---|---|---|
| 5,289,385 A * | 2/1994 | Grandone | ........................ 702/19 |
| 2003/0063142 A1 * | 4/2003 | Sakamoto et al. | ................. 347/5 |
| 2003/0235804 A1 | 12/2003 | Torabinejad et al. | |
| 2007/0054415 A1 * | 3/2007 | Muraishi | ....................... 436/518 |
| 2007/0175284 A1 | 8/2007 | Oonuma et al. | |
| 2008/0187990 A1 | 8/2008 | Nagai et al. | |

FOREIGN PATENT DOCUMENTS

| | | |
|---|---|---|
| CN | 1633261 A | 6/2005 |
| CN | 101013139 A | 8/2007 |
| CN | 101236194 A | 8/2008 |
| EP | 0359049 A2 | 3/1990 |
| EP | 1376138 A2 | 1/2004 |

(Continued)

OTHER PUBLICATIONS

Communication dated Jun. 18, 2014 from the European Patent Office in counterpart European Patent Application No. 09012003.1.

*Primary Examiner* — Kathryn Wright
(74) *Attorney, Agent, or Firm* — Sughrue Mion, PLLC

(57) ABSTRACT

The present invention is to present a sample processing apparatus, comprising: a sample processing mechanism which comprises a flow channel to be used for processing a sample, and performs a sample processing operation for processing the sample using the flow channel and a cleaning operation for cleaning the flow channel; and a controller for controlling the cleaning operation by the sample processing mechanism, based on an elapsed time since a previous cleaning operation by the sample processing mechanism.

19 Claims, 14 Drawing Sheets

(56) References Cited

FOREIGN PATENT DOCUMENTS

| | | |
|---|---|---|
| JP | 01-161155 A | 6/1989 |
| JP | 2000-276652 A | 10/2000 |
| JP | 2003-254980 A | 9/2003 |
| JP | 2006-009556 A | 1/2006 |
| JP | 2008-006138 A | 1/2008 |
| JP | 2008-201094 A | 9/2008 |
| WO | 9508774 A2 | 3/1995 |

* cited by examiner

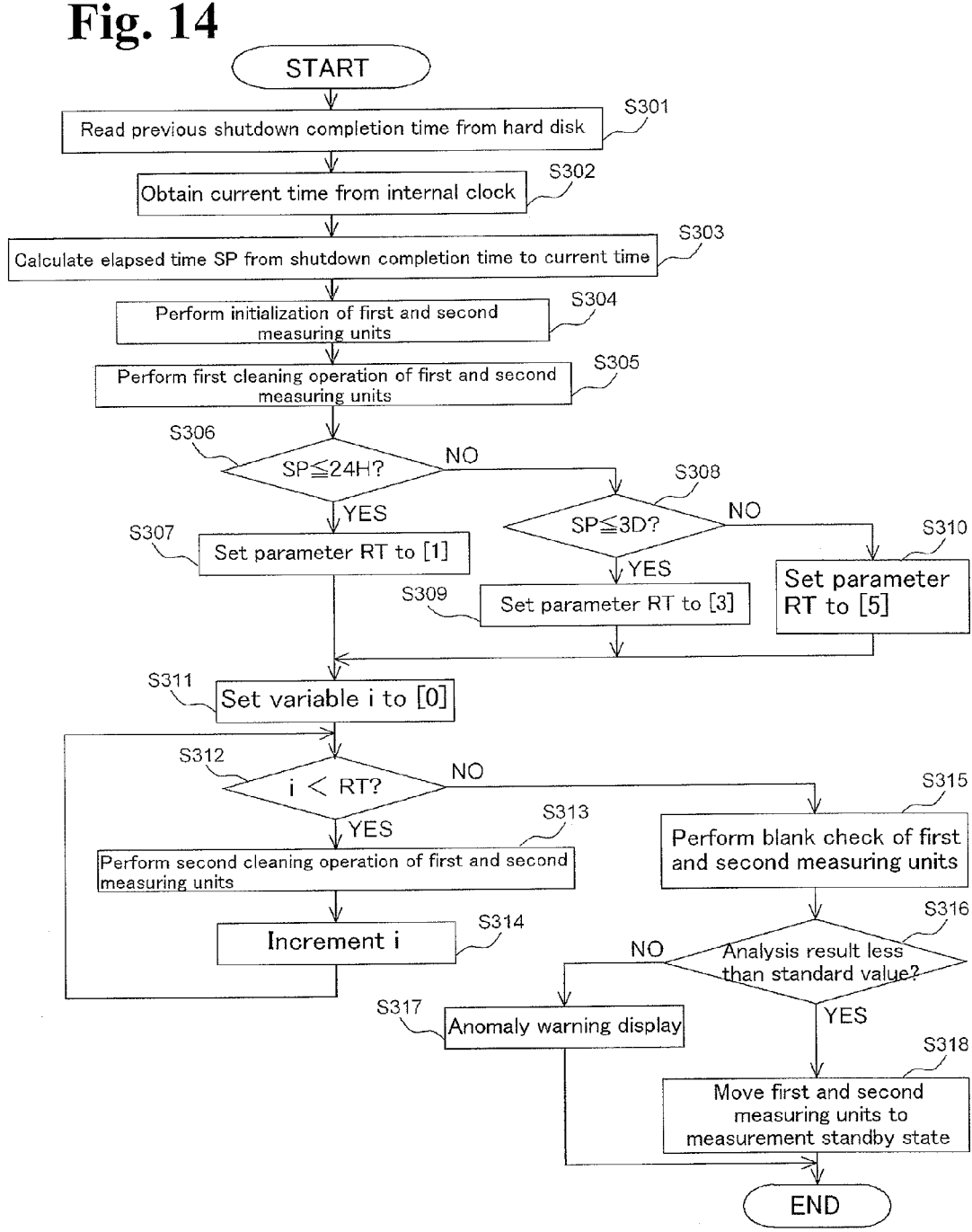

SAMPLE PROCESSING APPARATUS AND CLEANING METHOD

FIELD OF THE INVENTION

The present invention relates to a sample processing apparatus for processing a sample such as blood, urine and the like, and a cleaning method for cleaning a sample processing mechanism for processing a sample.

BACKGROUND

Various conventional sample analyzers are known, such as multi-item blood cell analyzers, blood coagulation measuring apparatuses, immunoanalyzers, biochemical analyzers, urine analyzers and the like.

Japanese Laid-Open Patent Publication No. H1-161155 discloses an automated analyzer for automatically turning ON a power supply at a preset time, heating a flow cell bath to a predetermined temperature, and automatically performing the operation of a water blank measurement or reagent blank measurement. Japanese Laid-Open Patent Publication No. H1-161155 further discloses a structure which is provided with an automatic cleaning mechanism for injecting a detergent into a pipette and reagent container and automatically performs cleaning operation after the power supply has been turned ON.

Prior to measuring a sample, dirt and air bubbles and the like must be removed since dirt and air bubbles may adhere to the automated analyzer and affect the measurement of the sample. When the automated analyzer performs the cleaning operation, dirt and air bubbles are prevented from influencing the measurement results. However, when a long time elapses since performing a cleaning operation, residual bacteria may breed and new air bubbles may form, thus causing concern that the measurement results may be influenced in such cases. The automated analyzer disclosed in Japanese Laid-Open Patent Publication No. H1-161155 executes a fixed cleaning operation after the power supply has been turned ON regardless of the time that has elapsed since the automated analyzer last performed a cleaning operation. Therefore, there is concern that the cleaning may be inadequate when a long time has elapsed since the previous cleaning.

SUMMARY

The first aspect of the present invention is a sample processing apparatus, comprising: a sample processing mechanism which comprises a flow channel to be used for processing a sample, and performs a sample processing operation for processing the sample using the flow channel and a cleaning operation for cleaning the flow channel; and a controller for controlling the cleaning operation by the sample processing mechanism, based on an elapsed time since a previous cleaning operation by the sample processing mechanism.

The second aspect of the present invention is a cleaning method for cleaning a flow channel of a sample processing mechanism which performs a sample processing operation for processing the sample using the flow channel and a cleaning operation for cleaning the flow channel, comprising steps of: (a) detecting an elapsed time since a previous-cleaning operation of the sample processing mechanism; and (b) controlling the cleaning operation by the sample processing mechanism based on the detected elapsed time.

BRIEF DESCRIPTION OF THE DRAWINGS

FIG. 14 is a flow chart showing the flow of the start-up operation of the sample analyzer.

DETAILED DESCRIPTION OF THE EMBODIMENT

The preferred embodiments of the present invention are described hereinafter with reference to the drawings.

The present embodiment is a sample analyzer for performing a cleaning operation of a sample processing mechanism based on the elapsed time since completion of a previous shutdown operation in the start-up operation performed immediately after the power supply is turned ON.

[Sample Analyzer Structure]

Figure 1A:
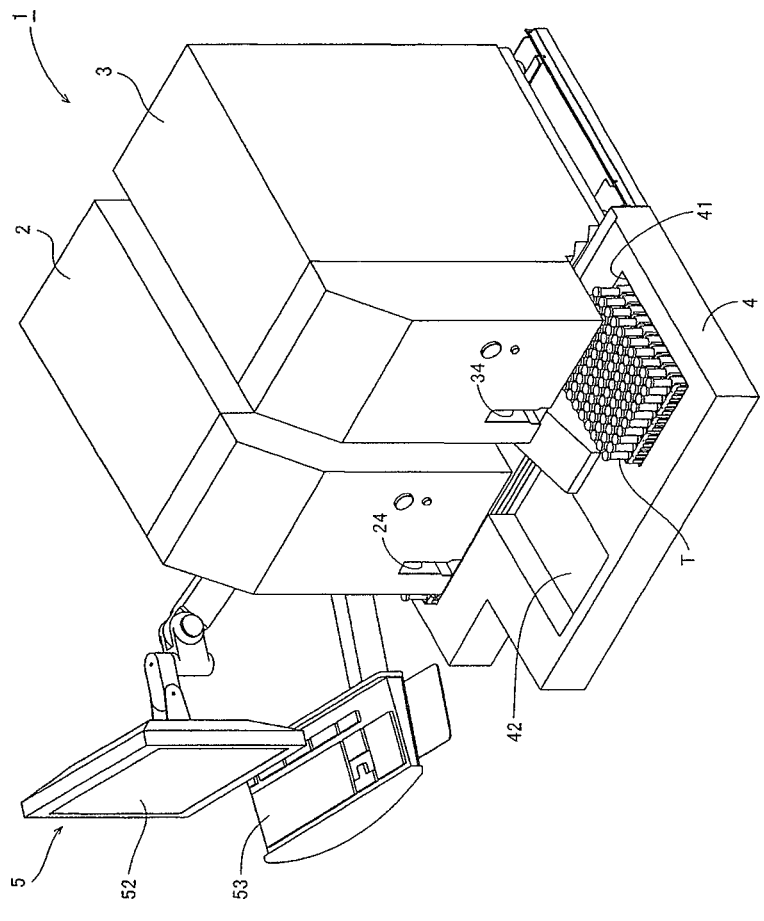
FIGS. 1A and 1B are perspective views showing the general structure of an embodiment of the sample analyzer.
Figure 1B:
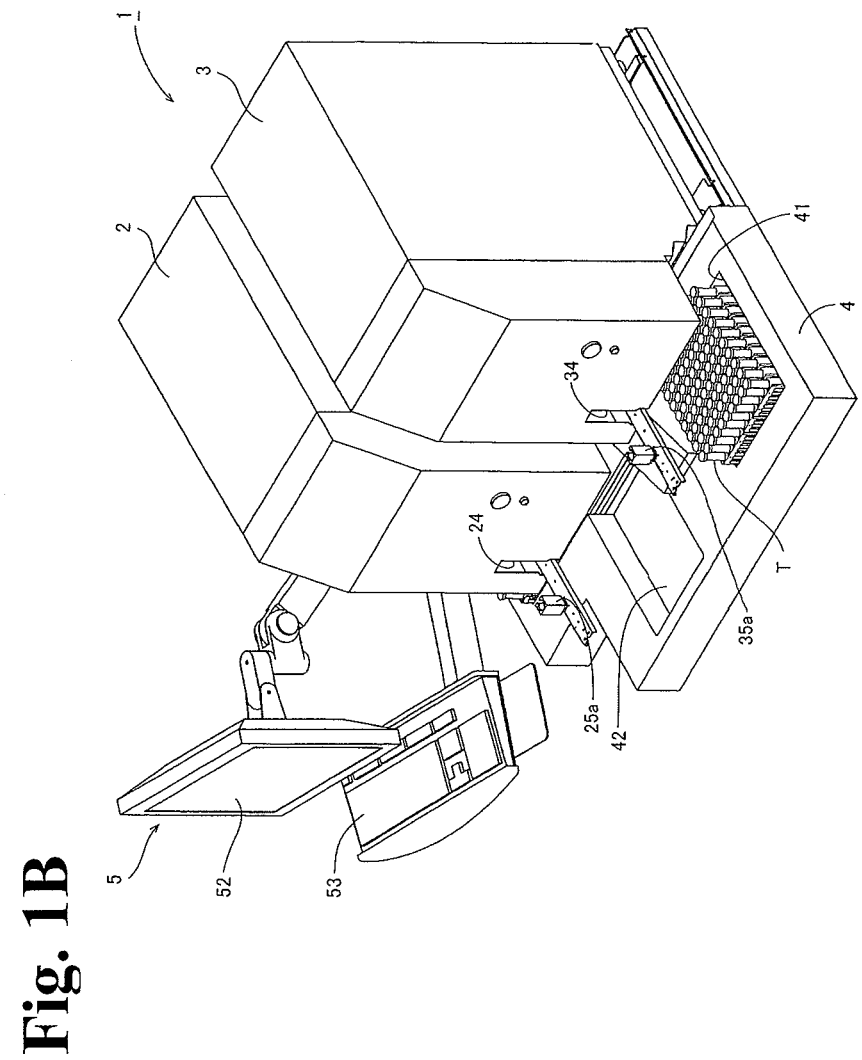

The sample analyzer 1 of the present embodiment is a multifunction blood cell analyzer which detects and counts the white blood cells, red blood cells, and platelets contained in a blood sample. As shown in FIGS. 1A and 1B, the sample analyzer 1 is provided with a first measuring unit 2, second measuring unit 5, sample transporting unit 4 disposed on the front side of the first measuring unit 2 and second measuring unit 5, and information processing unit 5 which is capable of controlling the first measuring unit 2, second measuring unit 5, and sample transporting unit 4.

Figure 2:
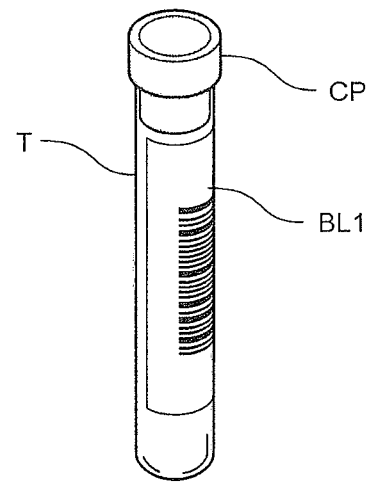
FIG. 2 is a perspective view showing the external appearance of a sample container.
Figure 3:
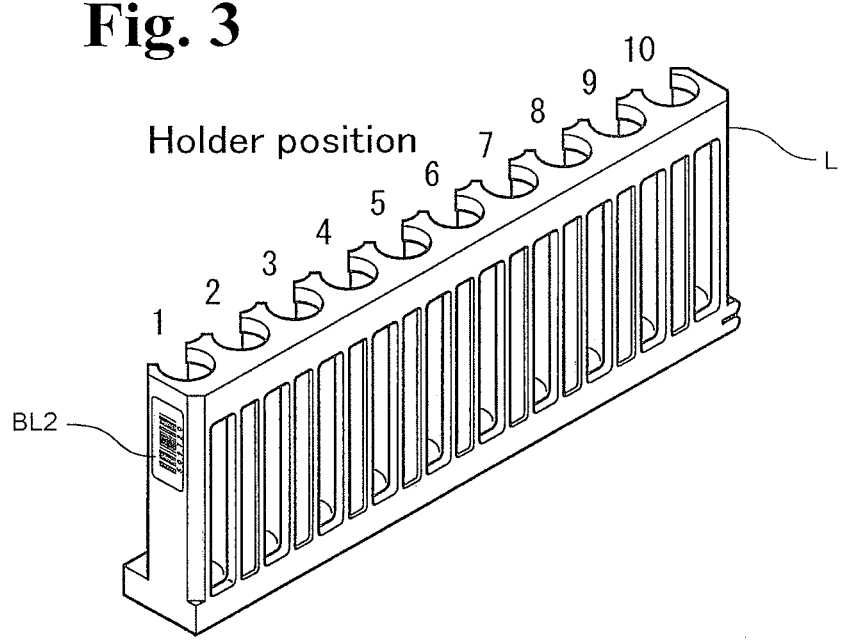
FIG. 3 is a perspective view showing the external appearance of a sample rack.

As shown in FIG. 2, a sample container T is tube-like with an open top end. A blood sample collected from a patient is contained within the container, and the opening at the top end is sealed by a cap CP. The sample container T is made of synthetic resin or glass capable of transmitting light, so that the blood sample contained within is visible. A barcode label BL1 is also adhered to the side surface of the sample container T. A barcode representing the sample ID is printed on the barcode label BL1. A sample rack L is capable of holding a row of ten sample containers T. Each sample container T is held in a vertical position (upright position) in the sample rack L. A barcode label BL2 is also adhered to the side surface of the sample rack L. A barcode representing the rack ID is printed on the barcode label BL2.

<Measuring Unit Structure>

Figure 4:
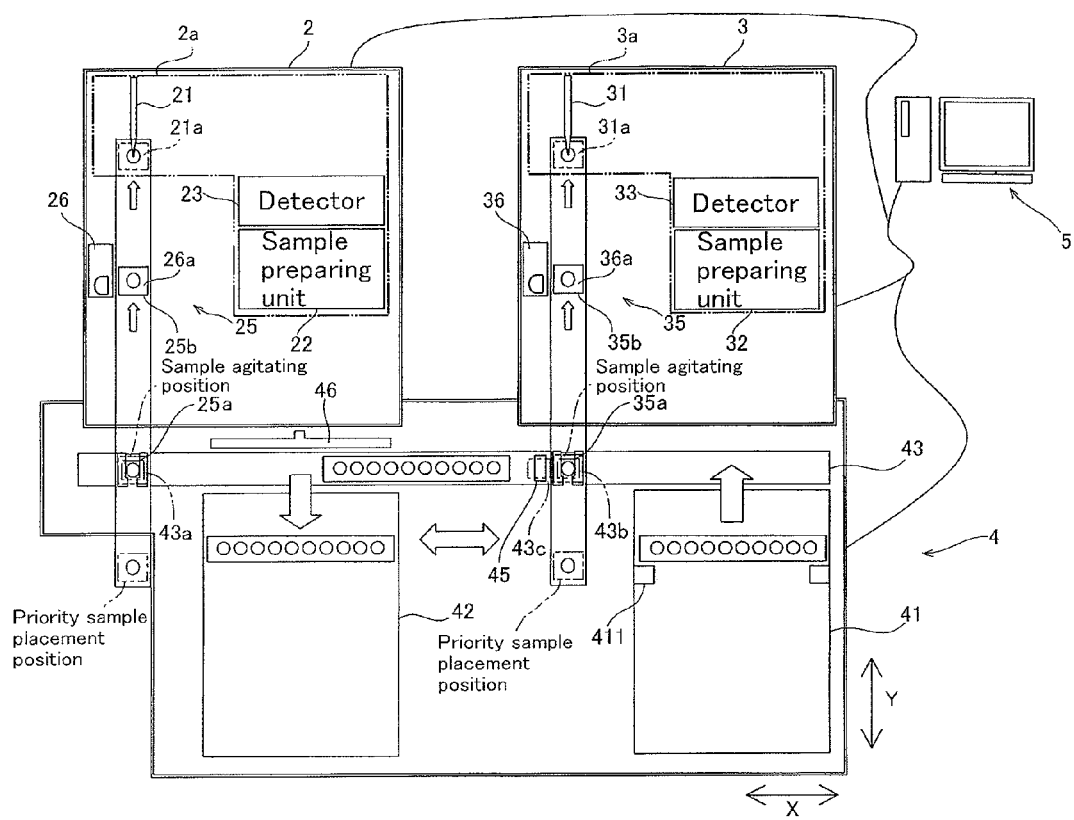
FIG. 4 is a block diagram showing the structure of the measuring unit of the embodiment.

The structure of the measuring unit is described below. Note that although the structure of the first measuring unit 2 is described below, the description is also pertinent to the structure of the second measuring unit 5 which is omitted since the structures of the first measuring unit 2 and the second measuring unit 5 are identical. Structural elements identical to the first measuring unit 2 are provided with the reference numbers corresponding to the first measuring unit 2. As shown in FIG. 4, the first measuring unit 2 has a measuring mechanism 2a configured by a sample aspirator 21 for aspirating a blood sample from a sample container (collection tube), sample preparing unit 22 for preparing a measurement sample for measuring from the blood aspirated by the sample aspirator 21, and a detecting unit 25 for detecting the blood cells from the measurement sample prepared by the sample preparing unit 22. The first measuring unit 2 also has a take-up door 24 (refer to FIGS. 1A and 1B) for taking into the first measuring unit 2 a sample container T held in a sample rack L conveyed by a rack conveyor 45 of the sample transporting unit 4, and a sample container conveyor 25 for taking the sample container T from the sample rack L into the first measuring unit 2 and transporting the sample container T to the aspirating position of the sample aspirator 21.

Figure 5A:
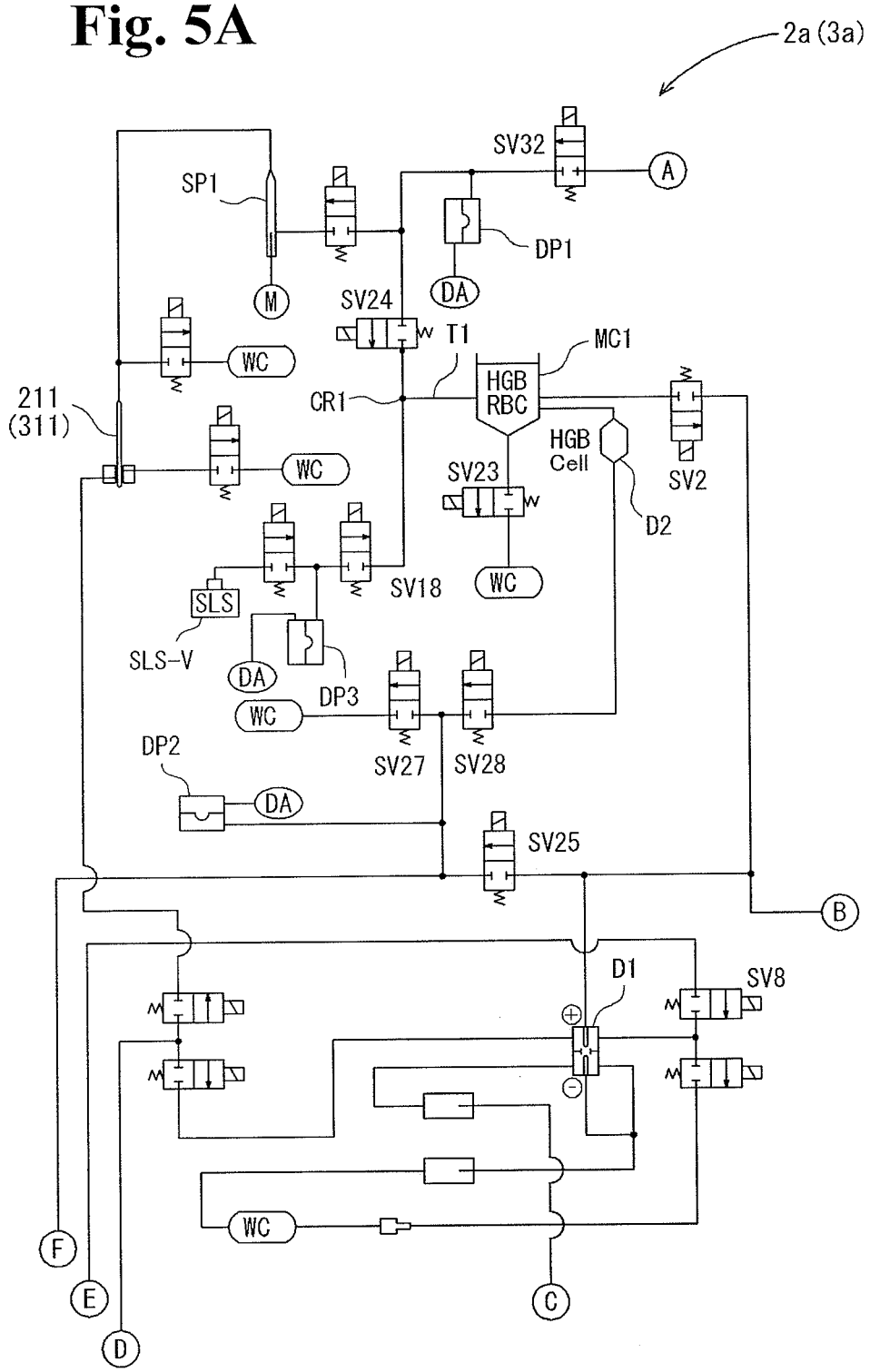
FIGS. 5A and 5B are fluid circuit diagrams showing the structure of the measuring mechanism.

As shown in FIG. 4, an aspirating tube 211 shown in FIG. 5A is provided on the tip of the sample aspirator 21. The sample aspirator 21 is also provided with a whole blood aspirating syringe pump SP1. The aspirating tube 211 is movable in vertical directions, and is configured so as to pass through the cap CP of the sample container T which has been transported to the aspirating position, and aspirate the blood from within the container T.

Figure 5B:
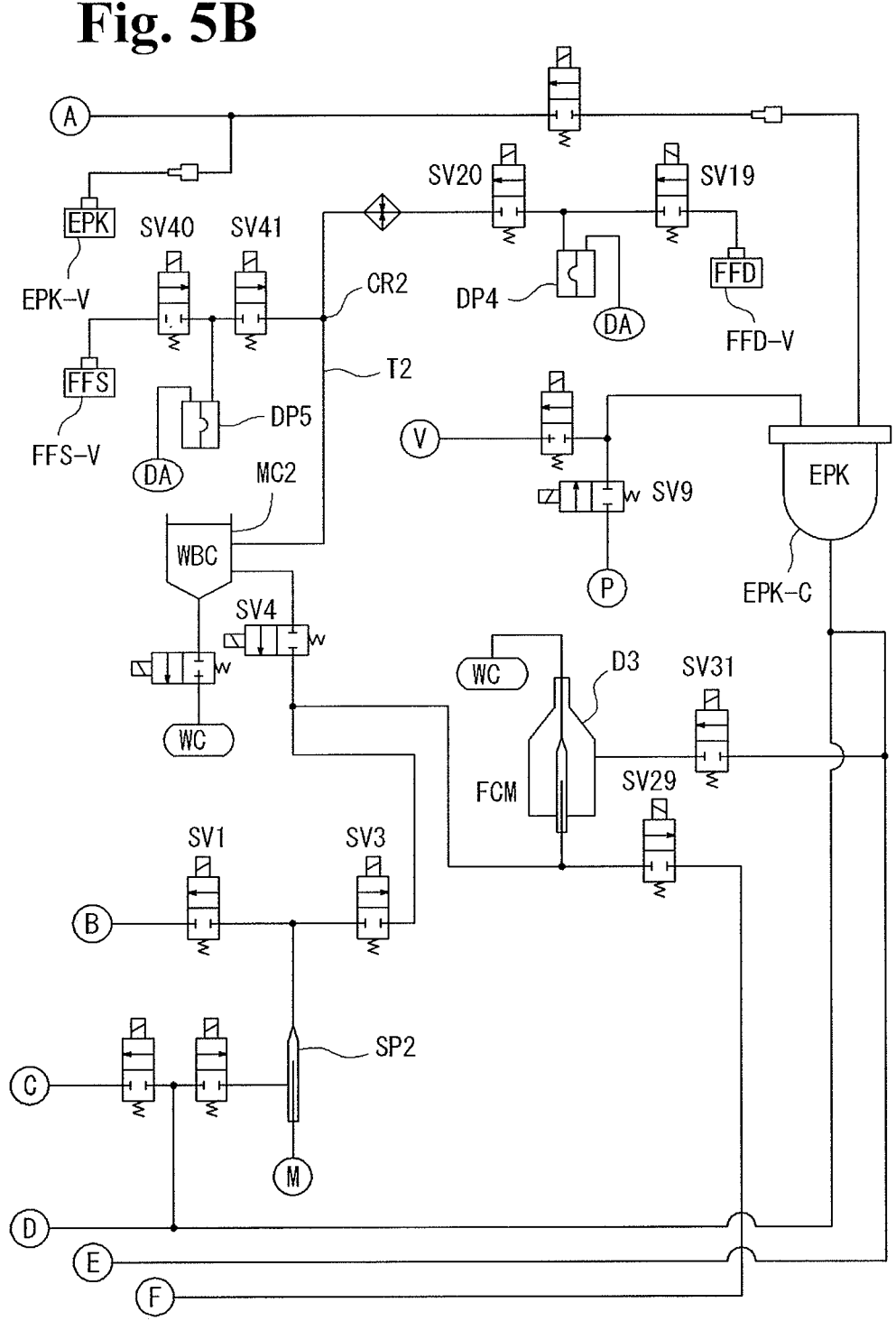

The sample preparing unit 22 is provided with a first mixing chamber MC1 (refer to FIG. 5A) and a second mixing chamber MC2 (refer to FIG. 5B). The aspirating tube 211 aspirates a predetermined amount of the whole blood sample from the sample container T via the whole blood aspirating syringe pump SP1, moves the aspirated sample to the positions of the first mixing chamber MC1 and second mixing chamber MC2, and allocates predetermined amounts of the whole blood sample to the respective mixing chambers MC1 and MC2 via the whole blood aspirating syringe pump SP1.

A reagent container accommodating reagent can be disposed in the first measuring unit 2, and the reagent container can be connected to the flow channel. Specifically, the reagent containers used in the present embodiment are a dilution liquid container EPK-V for accommodating dilution liquid (cleaning liquid) EPK, hemoglobin hemolytic agent container SLS-V for accommodating hemoglobin hemolytic agent SLS, white blood cell classifying hemolytic agent container (common reagent container) FFD-V for accommodating white blood cell classifying hemolytic agent FFD for dissolving red blood cells, and white blood cell classifying stain container (special reagent container) FFS-V for accommodating white blood cell classifying stain FFS (refer to FIGS. 5A and 5B).

Figure 5C:
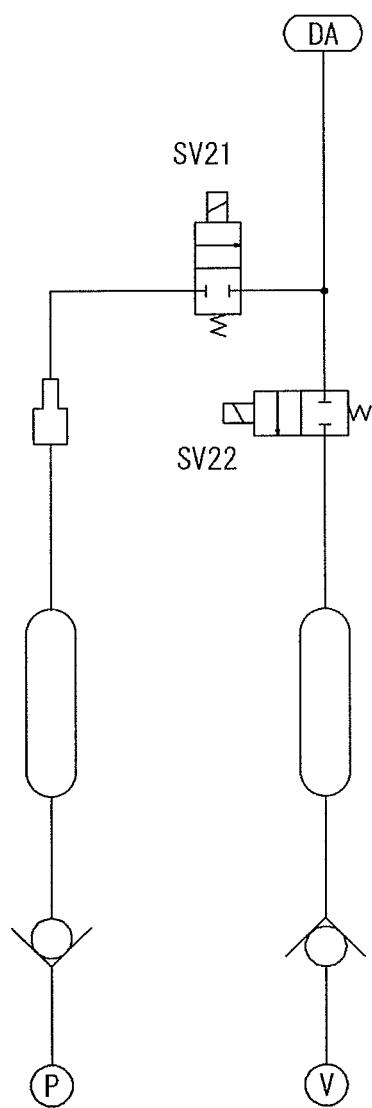
FIG. 5C is a fluid circuit diagram of the surroundings of the diaphragm pump.

The dilution liquid container EPK-V and hemolytic agent container SLS-V are connected so as to be capable of supplying reagent to the first mixing chamber MC1. That is, the dilution liquid can be supplied from the dilution liquid container EPK-V to the first mixing chamber MC1 via a dilution liquid supplying (EPK) diaphragm pump DP1; the dilution liquid supplying (EPK) diaphragm pump DP1 configures a dilution liquid reagent supplying section. Note that the diaphragm pumps DP1 through DP5 shown in FIGS. 5A and 5B are connected to a positive pressure source and negative pressure source through the electromagnetic valves SV21 and SV22 shown in FIG. 5C, and are configured so as to be driven by the positive pressure source and negative pressure source.

The hemolytic agent can also be supplied from hemolytic agent container SLS-V to the first mixing chamber MC1 via a hemolytic agent supplying (SLS) diaphragm pump DP5; the hemolytic supplying (SLS) diaphragm pump DP5 configures a hemolytic agent reagent supplying section.

The hemolytic agent container FFD-V and stain container FFS-V are connected so as to supply reagent to the second mixing chamber MC2. That is, the hemolytic agent can be supplied from the hemolytic agent container FFD-V to the second mixing chamber MC2 via a hemolytic agent supplying (FFD) diaphragm pump DP4; the hemolytic agent supplying (FFD) diaphragm pump DP4 configures a hemolytic agent reagent supplying section.

The stain can be supplied from the stain container FFS-V to the second mixing chamber MC2 via the stain (FFS) diaphragm pump DP5; the stain diaphragm pump DP5 configures a stain reagent supplying section.

The reagent supplying channel from the dilution liquid container EPK-V to the first mixing chamber MC1 and the reagent supplying channel from the hemolytic agent container SLS-V to the first mixing chamber MC1 are joined at a midway confluence point CR1, forming a common reagent supplying channel T1 for both reagents which is connected to the first mixing chamber MC1 (refer to FIG. 5A). The reagent supplying channel from the hemolytic agent container FFD-V to the second mixing chamber MC2 and the reagent supplying channel from the stain container FFS-V to the second mixing chamber MC2 are joined at a midway confluence point CR2, forming a common reagent supplying channel T2 for both reagents which is connected to the second mixing chamber MC2 (refer to FIG. 5B). Note that the reagent supplying channels T1 and T2 may also be provided for each reagent. That is, two reagent supplying ports may be provided for each chamber MC1 and MC2.

The detecting unit 25 is provided with a first detector D1 for performing measurements related to red blood cells and platelets, second detector D2 for performing measurements related to hemoglobin, and third detector D3 for performing measurements related to white blood cells.

The first mixing chamber MC1 is a component for preparing a measurement sample used to analyze red blood cells, platelets, and hemoglobin, and the measurement sample prepared by the first mixing chamber MC1 is used in measurements performed by the first detector D1 and second detector D2. The second mixing chamber MC2 is a component for preparing a measurement sample used to analyze white blood cells, and the measurement sample prepared by the second mixing chamber MC2 is used in measurements performed by the third detector D3.

The first detector D1 is configured as an RBC/PLT detector for performing RBC measurements (measuring red blood cell count), and PLT measurements (measuring platelet count). The RBC/PLT detector D1 can perform RBC and PLY measurements via a sheath flow DC detection method.

The second detector D2 is configured as an HGB detector for performing HGB measurements (measuring the amount of pigment in the blood). The HGB detector D2 can perform HGB measurements via an SLS-hemoglobin method.

The third detector D3 is configured as an optical detector capable of performing WBC measurements (white blood cell count), and DIFF measurements (white blood cell classifications). The optical detector D3 is configured so as to be capable of detecting WBC (white blood cells), NEIT (neutrophils), LYMPH (lymphocytes), EO (eosinophils), BASO (basophils), and MONO (monocytes) via flow cytometry using a semiconductor laser. The detecting unit 25 uses different detection methods for detecting WBC that does not involve detecting the five classifications of white cells, that is, for detecting MEUT, LYMPH, EO, BASO, and MONO classifications, and detecting WBC that does involve detecting the five classifications of WBC. When detecting WBC that does not involve detecting the five white blood cell classifications, a measurement sample composed of a mixture of sample, hemolytic agent, and dilution liquid is measured, and the obtained measurement data is analyzed by the information processing unit 5 to complete the WBC measurements. On the other hand, when detecting WBC that does involve the five classifications of white blood cells, a measurement sample composed of a mixture of sample, staining reagent, hemolytic agent, and dilution liquid is measured and the obtained measurement data are analyzed by the information processing unit 5 to measure NEUT, LYMPH, EO, BASO, MONO, and WBC.

Figure 6:
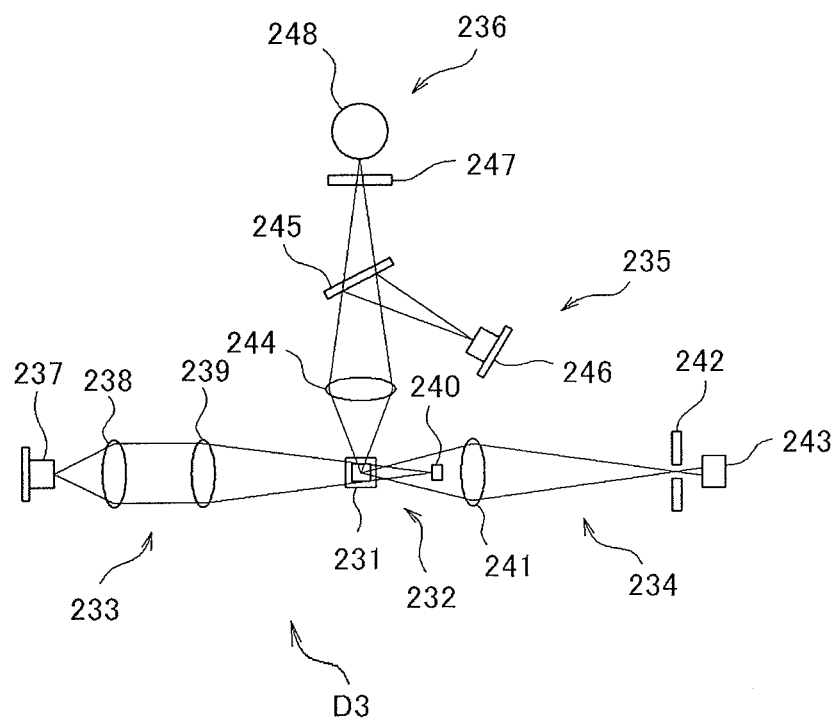
FIG. 6 is a schematic view showing the main structure of the optical detecting unit for WBC/DIFF (five categories of white blood cells) detection.

FIG. 6 shows the essential structure of the optical detector D3 used for WBC/DIFF (five classifications of WBC) detection. The optical detector D3 has a sheath flow system 252, beam spot forming system 255, forward scattered light receiving system 254, side scattered light receiving system 255, side fluorescent light receiving system 256; and a measurement sample is delivered to a flow cell 251, a liquid flow is generated within the flow cell 251, semiconductor laser light irradiates the blood cells contained in the liquid flow passing within the flow cell 251 and the blood cells are measured.

The sheath flow system 252 improves the accuracy and reproducibility of the blood cell counts by forming a single row of blood cells encapsulated in a sheath fluid which advances linearly within the flow cell 251. This arrangement is adopted due to reports of erroneous analysis results caused by the detection of air bubble particles mixed in the flow cell 251. The beam spot forming system 255 is configured so that the light emitted from a semiconductor laser 257 passes through a collimator lens 258 and condenser lens 259 to irradiate the flow cell 251. The beam spot forming system 255 also is provided with a beam stopper 240.

The forward scattered light receiving system 254 is configured so that the forward scattered light is collected by a forward collecting lens 241, and the light passing through a pinhole 242 is received by a photodiode (forward scattered light receiver) 245.

The side scattered light receiving system 255 collects the light scattered laterally via a side collective lens 244, and part of the light is reflected by a dichroic mirror 245 and received by a photodiode (side scattered light receiver) 246.

Light scattering is a phenomenon produced by the change ion the direction the light travels caused by the particles when particles such as blood cells in the direction of travel of the light are present as obstacles in the direction of travel of the light. Information relating to the size and material of the particle can be obtained by detecting the scattered light. In particular, information relating to the size of the particle (blood cell) can be obtained from the forward scattered light. Information relating to the interior part of the particle can also be obtained from the side scattered light. When laser light irradiates a blood cell particle, the intensity of the side scattered light is dependent on the complexity (shape, size, viscosity, and degree of granularity of the nucleus) of the cell interior. Thus, measurements in addition to the measurement of classes of white blood cells can be performed using the characteristic of the side scattered light intensity.

The side fluorescent light receiving system 256 is configured so that the light passing through the dichroic mirror 245 then passes through a beam splitter filter 247, and is received by a photomultiplier (fluorescent light receiver) 248.

When light irradiates a fluorescent material such as a stained blood cell, light is generated which has a wavelength that is longer than the wavelength of the irradiating light. The intensity of the fluorescent light is strong when the blood cell is deeply stained, so that information relating to the degree of staining of the blood cell can be obtained by measuring the fluorescent light intensity. Thus, measurements in addition to measuring the classes of white blood cells can be performed by the differences in the (side) fluorescent light intensity.

Returning now to FIG. 4, the structure of the sample container conveyor 25 is described below. The sample container conveyor 25 is provided with a hand 25*a* capable of holding the sample container T. The hand 25*a* is provided with a pair of mutually opposed grippers, which are capable of mutually coming together and separating. The grippers grasp the sample container T by coming together with the sample container T disposed therebetween. The sample container conveyor 25 can move the hand 25*a* in vertical directions and forward and back directions (Y direction), and can oscillate the hand 25*a*. Thus, a sample container T, which is positioned at the first sample supplying position 45*a* while disposed in the sample rack L, is grasped by the hand 25*a*, and the hand 25*a* is lifted upward to remove the sample container T from the sample rack L, whereupon the hand 25*a* is oscillated to agitate the sample within the sample container T.

The sample container conveyor 25 is also provided with a sample container holder 25*b* which has a hole for inserting a sample container T. After oscillation is completed, the sample container T held by the hand 25*s* as described above is then inserted into the sample container holder 25*b*. Thereafter, the sample container T is released by the hand 25*a* by causing the grippers to move apart, and the sample container T is placed in the sample container holder 25*b*. The sample container holder 25*b* is capable of moving horizontally in the Y direction via the motive force of a stepping motor which is not shown in the drawing.

A barcode reader 26 is provided within the first measuring unit 2. The sample container holder 25*b* can move to the barcode reading position 26*a* near the barcode reader 26, and the aspirating position 21*a* of the sample aspirator 21. When the sample container holder 25*b* has moved to the barcode reading position 26*a*, the held sample container T is rotated horizontally by a mechanism which is not shown in the drawing, whereupon the sample barcode is read by the barcode reader 26. Thus, the barcode label BL1 can be faced toward the barcode reader 26 by rotating the sample container T so as to allow the barcode reader 26 to read the sample barcode even when the barcode label BL1 of the sample container T is positioned on the opposite side of the container from the barcode reader 26. When the sample container holder 25*b* has moved to the aspirating position, the sample is aspirated from the held sample container T by the sample aspirator 21.

<Sample Transporting Unit Structure>

The structure of the sample transporting unit is described below. As shown in FIG. 1, the sample transporting unit 4 is disposed at the front of the first measuring unit 2 and second measuring unit 5 of the sample analyzer 1. The sample transporting unit 4 can transport a sample rack L to supply samples to the first measuring unit 2 and second measuring unit 5.

Figure 7:
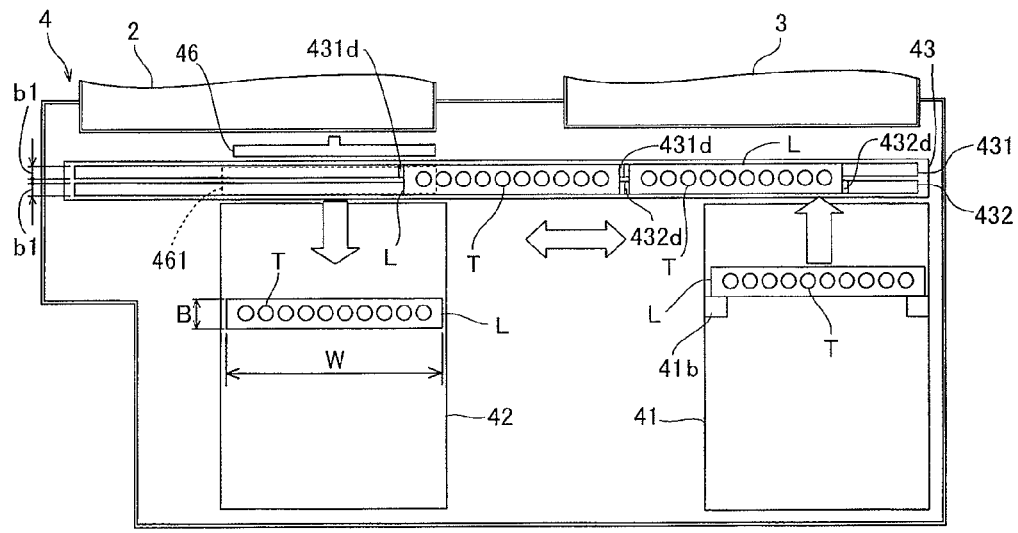
FIG. 7 is a plan view showing the structure of the sample transporting unit.

As shown in FIG. 7, the sample transporting unit 4 is configured by a pre-analysis holder 41 capable of temporarily holding a plurality of sample racks L which hold sample containers T containing sample before analysis, post-analysis rack holder 42 capable of temporarily holding a plurality of sample racks L holding sample containers T from which sample has been aspirated by the first measuring unit 2 or second measuring unit 5, and a rack conveyor 45 for linearly moving in a horizontal direction the sample racks L in the arrow X direction shown in the drawing to supply sample to the first measuring unit 2 or second measuring unit 5 and transporting the sample racks L received from the pre-analysis rack holder 41 to the post-analysis rack holder 42.

The pre-analysis rack holder 41 is square in shape when viewed from above, and the width is somewhat larger than the width of the sample rack L. The pre-analysis rack holder 41 becomes lower in stages from the circumferential surface, and the unanalyzed sample rack L is disposed on the top surface thereof. The rack mover 41b protrudes from both sides of the pre-analysis rack holder facing toward the inside. The sample rack L can be moved backward by the rack mover 41b engaging the sample rack L via the protrusion and moving backward in this condition (direction approaching the rack conveyor 45). The rack mover 41b is configured so as to be drivable by a stepping motor which is not shown in the drawing provided below the pre-analysis rack holder 41.

As shown in FIG. 7, the rack conveyor 45 is capable of moving the sample rack L, which has been transported by the pre-analysis rack holder 41, in the X direction. As shown in FIG. 4, a first sample supplying position 45a for supplying sample to the first measuring unit 2 and a second sample supplying position 45b for supplying sample to the second measuring unit 5 are present on the transporting path of the sample rack L moved by the rack conveyor 45. When the sample transporting unit 4 is controlled by the information processing unit 5 and transports the sample to the first sample supplying position 45a or the second sample transporting position 45b, the transported sample container T is grasped by the hand 25a or 55a of the corresponding measuring unit and the sample supplying is completed by removing the sample container T from the sample rack L, and the transporting of the sample rack L is suspended until the sample container is returned to the sample rack L. In this way the hand 25a or 55a can reliably remove the sample container T from the sample rack L while the sample container T is stopped at the first sample supplying position 45a or the second sample supplying position 45b. The rack conveyor 45 can also transport the sample rack L so as to move the sample container T to a sample container detecting position 45c.

Figure 8:
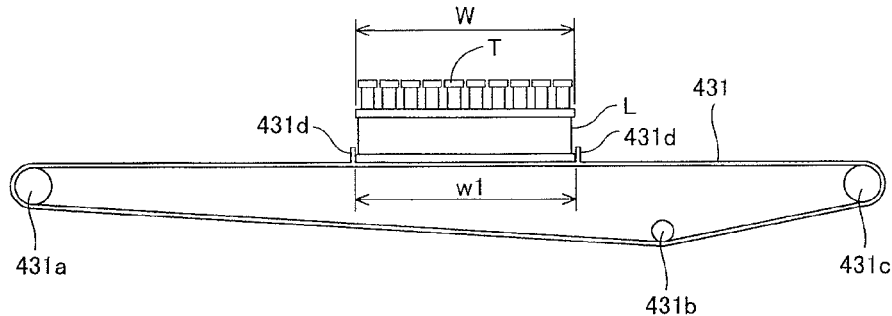
FIG. 8 is a front view showing the structure of a first belt of the sample transporting unit.
Figure 9:
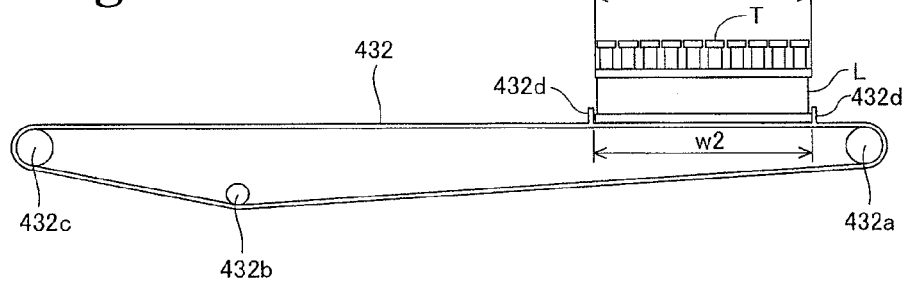
FIG. 9 is a front view showing the structure of a second belt of the sample transporting unit.

As shown in FIG. 7, the rack conveyor 45 has two belts including mutually independently operational first belt 451 and second belt 452. The widths b1 and b1 in the arrow Y direction of the first belt 451 and second belt 452 are less than one half the size of the width B in the arrow Y direction of the respective sample racks L. The first belt 451 and second belt 452 are disposed in parallel so as to not protrude from the width B of the sample rack L when the sample rack L is being transported by the rack conveyor 45. FIG. 8 is an elevation view showing the structure of the first belt 451, and FIG. 9 is an elevation view showing the structure of the second belt 452. As shown in FIGS. 8 and 9, the first belt 451 and second belt 452 are, respectively, endless belts, and the first belt 451 circumscribes rollers 451a through 451c, and the second belt 452 circumscribes rollers 452a through 452c. Two protrusions 451d are provided on the outer surface of the first belt 451 so as to have a slightly larger (for example, 1 mm) internal width w1 than the width W in the X direction of the sample rack L; similarly, two protrusions 452d are provided on the outer surface of the second belt 452 so as to have an inner width w2 approximately the same as the inner width w1. With the sample rack L held on the inner side of the two protrusions 451d, the first belt 451 moves the sample rack L in the arrow X direction by moving the outer surface of the rollers 451a through 451c via a stepping motor (not shown in the drawing). With the sample rack L held on the inner side of the two protrusions 452d, the second belt 452 moves the sample rack L in the arrow X direction by moving the outer surface of the rollers 452a through 452c via a stepping motor (not shown in the drawing). The first belt 451 and second belt 452 are also configured so as to transport the sample rack L with mutual independence.

A sample container sensor 45 is provided on the transport path of the rack conveyor 45. The sample container sensor 45 is a contact-type sensor, which has a // contact piece, light-emitting element for emitting light, and light-receiving element (not shown in the drawing). The Ample container sensor 45 is configured so that the contact piece is deformed via contact with a detection object, with the result that the light emitted from the light-emitting element is reflected by the contact piece and impinges the light-receiving element. In this way the contact piece is bent by the sample container T so that the sample container T can be detected when the sample container T detection object held in the sample rack L passes under the sample container sensor 45.

A rack conveyor 46 is disposed so as to face the post-analysis rack holder 42 (described later) sandwiching the rack conveyor 45. The rack conveyor 46 is configured so as to move linearly and horizontally in the arrow Y direction via the motive force of a stepping motor which is not shown in the drawing. In this way when a sample rack L has been moved to a position 461 (referred to as the "post-analysis rack transport position") between the post-analysis rack holder 42 and the rack conveyor 46, the sample rack L is pushed into the post-analysis rack holder 42 by moving the rack conveyor 46 to the post-analysis rack holder 42 side.

The post-analysis rack holder 42 is square in shape when viewed level, and the width is somewhat larger than the width of the sample rack L. The post-analysis rack holder 42 becomes lower in stages from the circumferential surface, and the analyzed sample rack L is disposed on the top surface thereof. The post-analysis rack holder 42 is connected to the previously mentioned rack conveyor 45, and the sample rack L fed from the rack conveyor 45 by the rack conveyor 46.

According to the above configuration, the sample transporting unit 4 moves a sample rack L positioned in the pre-analysis rack holder 41 to the rack conveyor 45, then the sample is supplied to the first measuring unit 2 or second measuring unit 5 by moving the sample rack L via the rack conveyor 45. The sample rack L holding the aspirated sample is then moved to the post-analysis rack transport position 461 by the rack conveyor 45 and delivered to the post-analysis rack holder 42 by the rack conveyor 46. When a plurality of sample racks L are disposed at the pre-analysis rack holder 41, the sample racks L containing analyzed samples are moved one by one to the post-analysis rack holder 42 by the rack conveyor 46, and the plurality of sample rack L are retained by the post-analysis rack holder 42.

<Information Processing Unit Structure>

Figure 10:
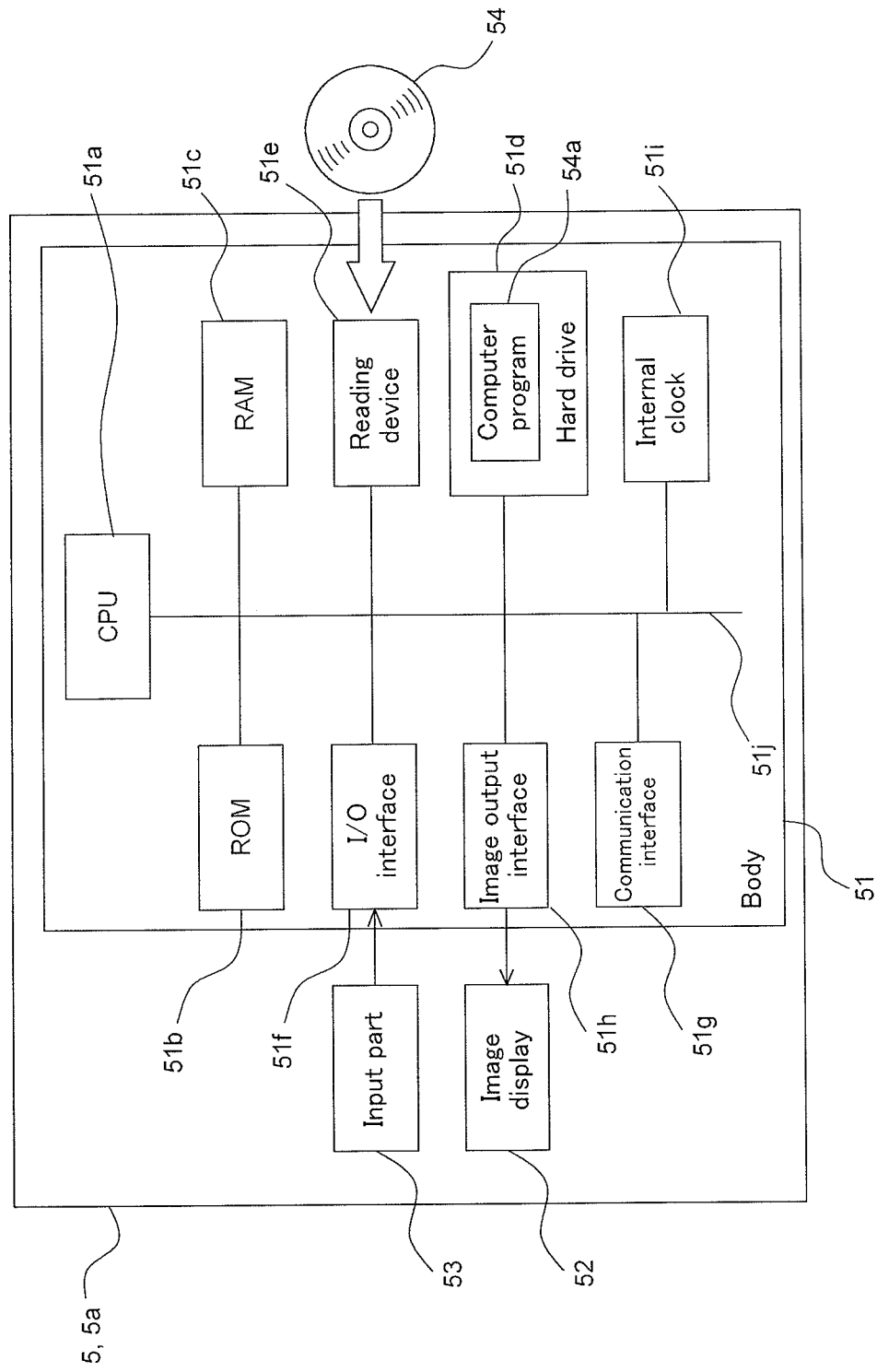
FIG. 10 is a block diagram showing the structure of the information processing unit of the embodiment.

The structure of the information processing unit is described below. The information processing unit 5 is configured by a computer. FIG. 10 is a block diagram showing the structure of the information processing unit 5. The information processing unit 5 is realized by a computer 5a. As shown in FIG. 10, the computer 5a is provided with a body 51, image display 52, and input part 55. The body 51 is configured by a CPU 51a, ROM 51b, RAM 51c, hard disk 51d, reading device 51e, input/output (I/O) interface 51f, communication interface 51g, image output interface 51h, and internal clock 51i; and the CPU 51a, ROM 51b, RAM 51c, hard disk 51d, reading device 51e, input/output (I/O) interface 51f, communication interface 51g, image output interface 51h, and internal clock 51i are connected by a bus 51j.

The CPU 51a is capable of executing computer programs loaded in the RAM 51c. The computer 5a functions as the information processing unit 5 when the CPU 51a executes a computer program 54a for controlling the first measuring unit 2 and second measuring unit 5 as well as for the sample analysis which is described later.

The ROM 51b is configured by a mask ROM, PROM, EPROM, EEPROM or the like, and records the computer programs to be executed by the CPU 51a as well as the data used by those computer programs.

The RAM 51c is configured by SRAM, DRAM or the like. The RAM 51c is used when reading the analysis program 54a recorded on the hard disk 51d. The RAM 51c is also used as the work area of the CPU 51a when the CPU 51a executes computer programs.

The hard disk 51d stores an operating system, application programs and the like, and the various computer programs to be executed by the CPU 51a as well as the data used in the execution of the computer programs. Also installed on the hard disk 51d is the computer program 54a which is described later. The computer program 54a is an event-driven type of computer program.

The reading device 51e is configured by a floppy disk drive, CD-ROM drive, DVD-ROM drive or the like, and is capable of reading computer programs or data recorded on a portable recording medium 54. The portable recording medium 54 stores the analysis program 54a which enables the computer to function as the information processing unit 5, so that the computer 5a can read the analysis program 54a from the portable recording medium 54, and install the analysis program 54a on the hard disk 51d.

Note that the computer program 54a can not only be provided by the portable recording medium 54, the computer program 54a may also provided over an electrical communication line from an external device which is connected to the computer 5a via the electrical communication line (either wireless or wired) so as to be capable of communication. For example, the computer program 54a may be stored on the hard disk of a server computer on the Internet so that the computer 5a can access the server computer, download the computer program, and install the computer program on the hard disk 51d.

A multitasking operating system such as Microsoft Windows (registered trademark of Microsoft Corporation, USA) may also be installed on the hard disk 51d. In the following description, the computer program 54a of the present embodiment also operates on this operating system.

The I/O interface 51f may be a serial interface such as, for example, a USB, IEEE 1394, RS-232C or the like, a parallel interface such as a SCSI, IDE, IEEE 1284 or the like, and an analog interface configured by an D/A converter, A/D converter or the like. The input part 55 configured by a keyboard and mouse is connected to the I/O interface 51f so that a user may use the input part 55 to input data to the computer 5a. The I/O interface 51f is connected to the first measuring unit 2, second measuring unit 3, and sample transporting unit 4. Thus, the information processing unit 5 is capable of controlling the first measuring unit 2, second measuring unit 3, and sample transporting unit 4.

The communication interface 51g is an Ethernet (registered trademark) interface. The communication interface 51g is connected to a host computer not shown in the drawing through a LAN. The computer 5a can send and receive data to and from the host computer which is connected to the LAN by using a predetermined communication protocol through the communication interface 51g.

The image output interface 51h is connected to the image display 52 which is configured by an LCD, CRT or the like, and outputs image signals corresponding to the image data from the CPU 51a to the image display 52. The image display 52 displays images (screens) according to the input image signals.

The internal clock 51i outputs the current time. The CPU 51a obtains the current time from the internal clock 51i.

[Measuring Operation of the Sample Analyzer 1]

The operation of the sample analyzer 1 of the present embodiment is described below.

<Sample Measuring Operation>

The sample measuring operation performed by the sample analyzer 1 of the present embodiment is first described below. The sample analyzer 1 is capable of performing the CBC+DIFF measurement using the first detector D3, the RBC/PLT measurement using the first detector D1, and the HGB measurement using the second detector D2.

CBC+DIFF Measurement

The CBC+DIFF measurement is first described below. In the CBC+DIFF measurement, the sample analyzer 1 prepares a CBC+DIFF measurement sample by mixing a whole blood sample (11 µL), white blood cell classifying hemolytic agent (1 mL), and white blood cell classifying stain (20 µL), and measuring the CBC+DIFF measurement sample by flow cytometry using the optical detector D3. This measurement is performed by performing a white blood cell count measurement and measurement of the five white blood cell classifications.

Figure 11:
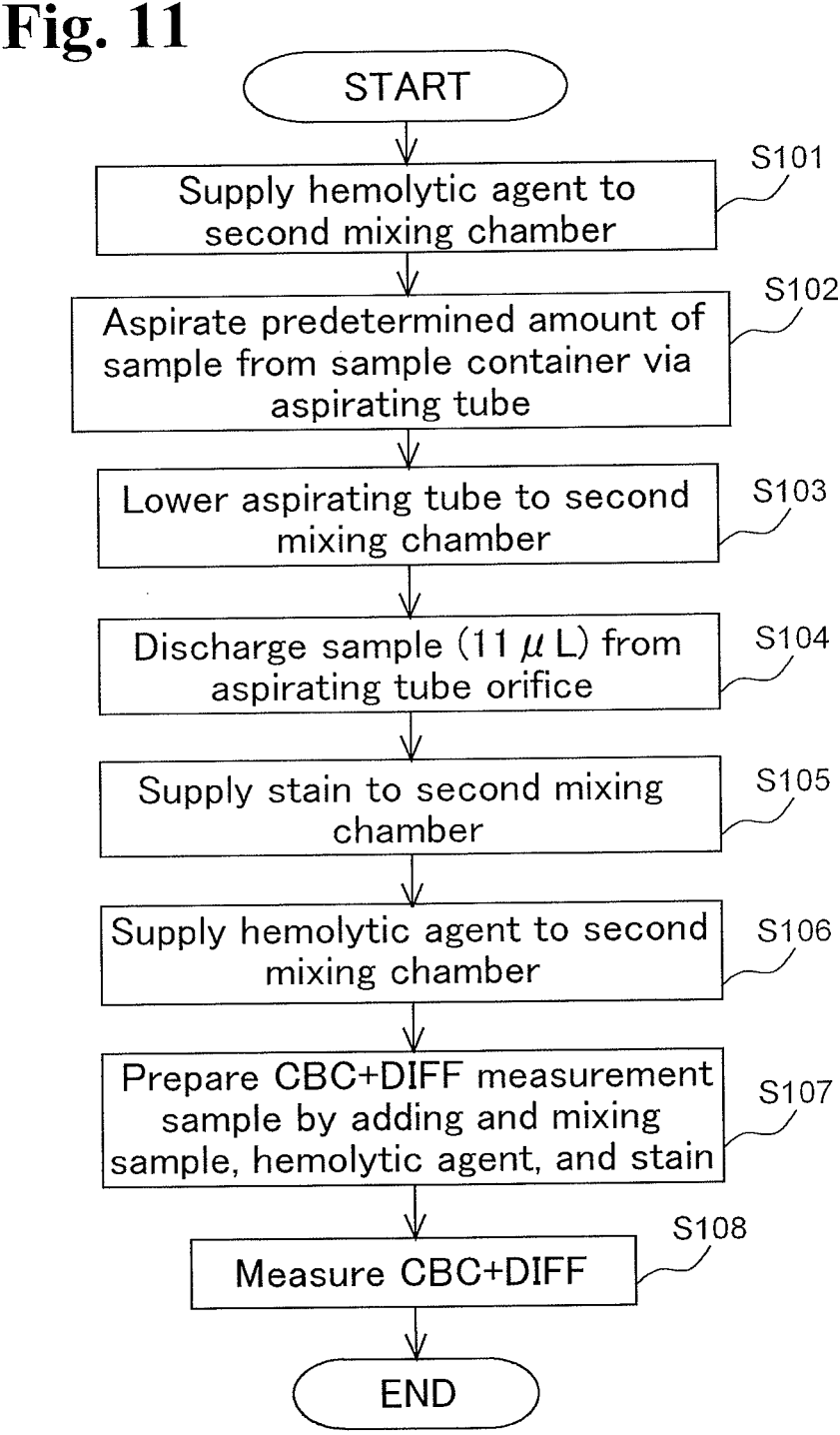
FIG. 11 is a flow chart showing the sequence of the operations of the sample analyzer during the CBC+DIFF measurement.

FIG. 11 is a flow chart showing the sequence of the operation of the sample analyzer 1 in the CBC+DIFF measurement. The hemolytic agent FDD (0.5 mL) is first supplied from the hemolytic agent container FDD-V to the second mixing chamber MC2 (step S101). Specifically, in the process of step S101 the FDD diaphragm pump D4 is driven with negative pressure and 0.5 mL of the hemolytic agent FDD is supplied from the hemolytic agent container FDD-V to the FDD diaphragm pump DP4 by opening the valve SV19 and closing the valve SV20 while opening the valve SV22 and closing the valve SV21. Then, the FDD diaphragm pump D4 is driven in positive pressure and 0.5 mL of hemolytic FDD is supplied to the second mixing chamber MC2 by the diaphragm pump D4 by closing the valve SV19 and opening the valve SV 20 while opening the valve SV21 and closing the valve SV22. Next, 0.5 mL of the hemolytic agent FDD is again supplied from the hemolytic agent container FDD-V to the FDD diaphragm pump D4 by driving the FDD diaphragm pump D4 with a negative pressure by opening the valve SV10 and closing the valve SV20 while closing the valve SV21 and opening the valve SV22.

A predetermined amount of the whole blood sample is then aspirated from the sample container T by the aspirator tube 211 (step S102). Specifically, the process of step S102 inserts the aspirating tube 211 into the sample container T and aspirates a predetermined amount (20 µL) of the whole blood sample by driving the whole blood aspirating syringe pump P1. The aspirating tube 211 is then removed from the sample container T, and the aspirating tube 211 is lowered to the second mixing chamber MC2 (step S103). From the aspirating orifice of the aspirating tube 211, 11 µL of whole blood sample (the part of the sample aspirated in step S102) is discharged into the second mixing chamber MC2 by driving the whole blood aspirating syringe pump while in this state (step S104).

After discharge, the stain FFS is introduced into the second mixing chamber MC2 (step S105). Specifically, in step S105 the stain supplying diaphragm pump (FFS diaphragm pump) DP5 is driven with negative pressure to supply 20 μL of stain FFS to the FFS diaphragm pump DP5 by opening the valve SV22 and closing the valve SV21 when the stain supplying valve SV40 is opened state and the stain supplying valve SV41 is closed state. Then the 20 (L of stain FFS is introduced into the second mixing chamber MC2 by driving the FFS diaphragm pump DP5 with positive pressure and opening the valve SV41 and closing the valve SV40 while opening the valve SV21 and closing the valve SV22.

The stain FFD is then introduced into the second mixing chamber MC2 (step S106). That is, the valves SV22 and SV19 are closed, the valves SV21 and SV21 are opened, and the FFD diaphragm pump DP4 is used to introduce 0.5 mL of hemolytic agent FFD into the second mixing chamber MC2, and the whole blood sample is introduced and mixed therewith to prepare the CBC+DIFF measurement sample in which the red blood cells are dissolved and the white blood cells are stained within the second mixing chamber MC2 (step S107).

The CBC+DIFF measurement is then performed by the WBC detector D3 using the CBC+DIFF measurement sample (step S108). Specifically, in the process of step S108 the valves SV4, SV29, and SV22 are opened, and valve SV21 is closed, then the charging diaphragm pump DP2 is driven and the CBC+DIFF measurement sample is accurately charged to 1.0 mL. The valves SV4, SV29, and SV22 are then closed and the charging to the WBC detector D3 is complete. Thereafter, the valves SV9 and SV31 are opened to supply the sheath fluid (dilution liquid) EPK from the EPK container EPK-C to the WBC detector. Then, with the valve SV1 in the closed state, the valve SV3 is opened and the sample supplying syringe pump SP2 is driven, and the measurement is performed in the WBC detector D3. The CBC+DIFF measurement operation thus ends.

The output signals (analog signals) from the WBC detector D3 are converted to digital signals by an A/D converter which is not shown in the drawing, the digital signals are then subjected to signal processing by a signal processing circuit which is not shown in the drawing to convert the digital data to measurement data, and the measurement data are then transmitted to the information processing unit 5. The CPU 51a of the information processing unit 5 generates analysis result data which includes the NEUT, LYMPH, EO, BASO, MONO, and WBC count data by subjecting the measurement data to predetermined analysis processing, and the analysis result data are then stored on the hard disk 51d.

RBC/PLT Measurement

The RBC/PLT measurement is described below. The RBC/PLT measurement and the HGB measurement, which will be described later, are performed in parallel with the previously described CBC+DIFF measurement.

Figure 12:
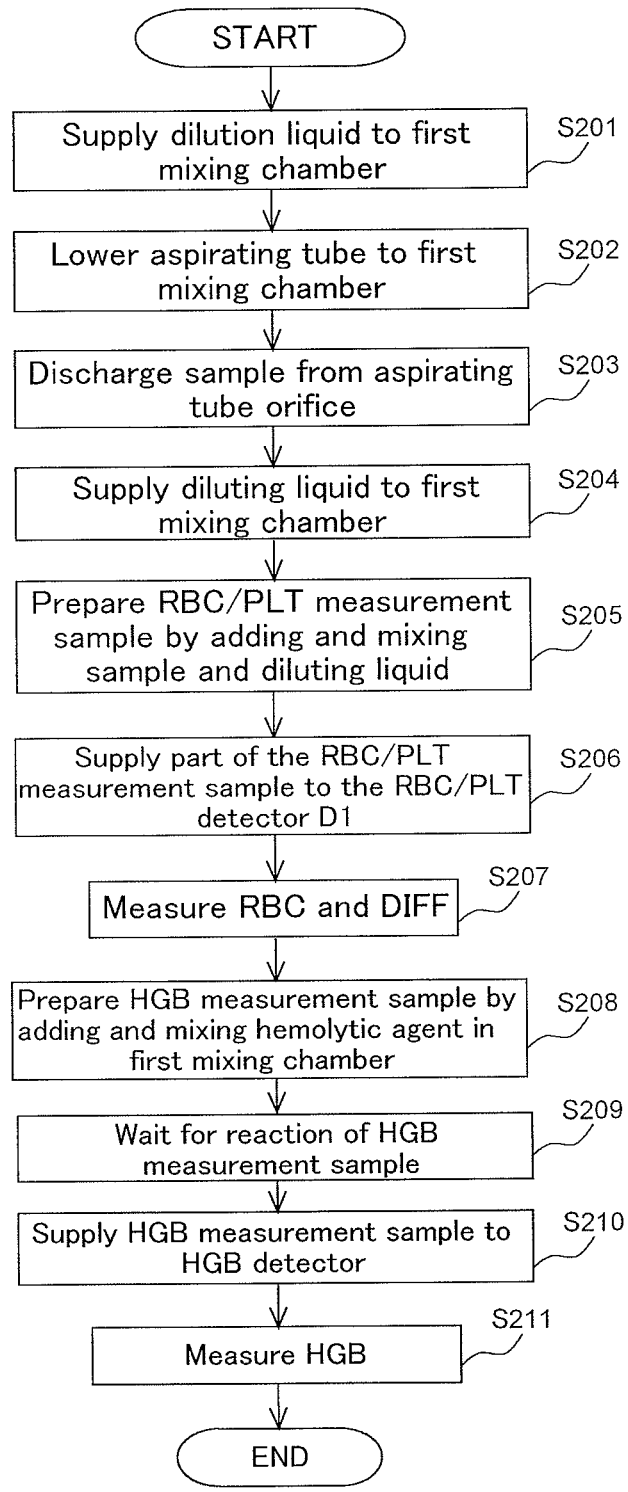
FIG. 12 is a flow chart showing the sequence of the operations of the sample analyzer during the RBC/PLT measurement and HGB measurement.

FIG. 12 is a flow chart showing the sequence of the operation of the sample analyzer 1 in the RBC/PLT measurement and HGB measurement. In step S102 (refer to FIG. 11), a predetermined amount (20 (L) of whole blood sample is aspirated from the sample container T by the aspirating tube (piercer) 211. Specifically, the aspirating tube 211 is inserted into the sample container T, and the whole blood aspirating syringe pump SP1 is driven to aspirate a predetermined amount of the whole blood sample. Thereafter, the diluting liquid EPK is supplied to the first mixing chamber MC1 (step S201). Specifically, in the process of step S201 the valve SV25 is operated for approximately 1.0 sec to discharge the liquid into the first mixing chamber MC1. Then the valves SV21 and SV24 are opened, and 1.0 mL of diluting liquid EPK is supplied to the first mixing chamber MC1 using the diluting liquid (EPK) diaphragm pump DP1, which has been resupplied diluting liquid EPK beforehand. Thereafter, the valves SV21 and SV24 are closed and the valves SV22 and SV32 are opened to resupply diluting liquid EPK to the EPK diaphragm pump DP1.

Then the aspirating tube 211 is lowered to the first mixing chamber (step S202), and 4 (L of whole blood sample is discharged from the aspirating orifice of the aspirating tube 211 into the first mixing chamber MC1 (step S203). Note that the processes of steps S202 and S203 are performed immediately after performing step S104 (refer to FIG. 11).

After the discharge is completed, the diluting liquid EPK is resupplied to the first mixing chamber MC1 (step S204). Specifically, in the process of step S204 after discharge completion, the valves SV22 and SV32 are closed and valves SV21 and SV24 are opened to resupply 1.0 mL of diluting liquid EPK to the first mixing chamber MC1 using the EPK diaphragm pump DP1. a first mixed sample (RBC/PLT measurement mixed sample) is thus prepared by mixing the whole blood sample (4 (L) and the diluting liquid (2 mL) inside the first mixing chamber MC1 (step S205). Note that after preparing the first mixed sample, the valves SV21 and SV24 are closed and the valves SV22 and SV32 are opened to resupply the diluting liquid EPK to the EPK diaphragm pump.

Next, part of the first mixed sample (RBC/PLT measurement mixed sample) is supplied to the RBC/PLT detector D1 (step S206). Specifically, in the process of step S206, 1.0 mL (part of the first mixed sample in the first mixing chamber MC1) is accurately charged in the flow channel between the first mixing chamber MC1 and the RBC/PLT detector D1 by opening the valves SV2 and SV25 using the charging diaphragm pump DP2. Then the valves SV2, SV25, SV22, and SV32 are closed and charging is complete. Valves SV8 and SV9 are then opened, and sheath fluid is supplied to the RBC/PLT detector D1.

Then the charged first mixed sample is supplied to the RBC/PLT detector D1, and the RBC/PLT measurement is performed (step S207). Specifically, in the process of step S207 the valve SV1 is opened and the sample supplying syringe pump SP2 is driven to supply the charged first mixed sample in the flow path to the RBC/PLT detector D1, and the RBC/PLT measurement is then performed by the RBC/PLT detector D1. The RBC/PLT measurement operation thus ends.

The output signals (analog signals) from the RBC/PLT detector D1 are converted to digital signals by an A/D converter which is not shown in the drawing, the digital signals are then subjected to predetermined signal processing by a signal processing circuit which is not shown in the drawing to convert the digital data to measurement data, and the measurement data are then transmitted together with the CBC+DIFF measurement data to the information processing unit 5. The CPU 51a of the information processing unit 5 generates analysis result data which includes the RBC and PLT count data by performing predetermined analysis processing of the measurement data, then stores the analysis result data on the hard disk 51d.

HGB Measurement

Even when the RBC/PLT measurement is completed, 1 mL of the first mixed sample remains as a residual sample in the first mixing chamber MC1. Hemolytic agent SLS is supplied to the first mixing chamber MC1 containing the residual sample to prepare a second mixed sample, that is, the HGB measurement mixed sample (step S208). Specifically, in the process of step S208, the hemolytic agent SLS is supplied to the first mixing chamber MC1 by opening the valves SV21 and SV18, and driving the hemoglobin hemolytic agent (SLS) diaphragm pump DP3 which has already been resupplied with hemolytic agent SLS. Thus, the hemolytic agent SLS and the first mixing sample are agitated to prepare the HGB measurement mixed sample (second mixed sample) containing a mixture of the first mixed sample (1.0 mL) and hemolytic agent SLS (0.5 mL).

The reaction of the HGB measurement mixed sample is awaited (step S209). During the optional time waiting for the reaction, the valves SV21 and SV27 are opened, the charging diaphragm pump DP2 is discharged, and the next charge is prepared.

Then, the valves SV22 and SV28 are opened, and charging of the HGB measurement mixed sample begins to the HGB detector D2, after which the valves SV22 and SV28 are closed and the charging is completed (step S210). The HGB measurement is then performed (step S211). The HGB measurement operation thus ends.

The output signals (analog signals) from the HGB detector D2 are converted to digital signals by an A/D converter which is not shown in the drawing, the digital signals are then subjected to signal processing by a signal processing circuit which is not shown in the drawing to convert the digital data to measurement data, and the measurement data are then transmitted together with the previously mentioned CBC+DIFF measurement data and RBC/PLT measurement data to the information processing unit 5. The CPU 51a of the information processing unit 5 generates analysis result data which includes the HGB count data by performing predetermined analysis processing of the measurement data, then stores the analysis result data on the hard disk 51d.

<Shutdown Operation>

Figure 13:
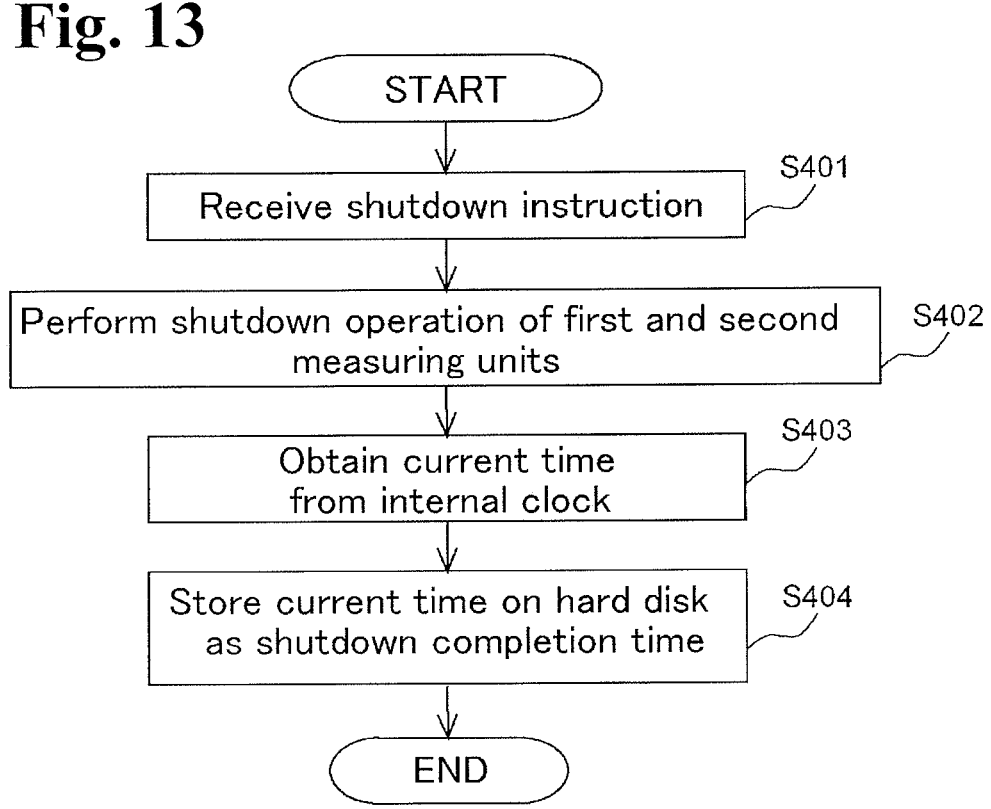
FIG. 13 is a flow chart showing the flow of the shutdown operation of the sample analyzer.

FIG. 13 is a flow chart showing the flow of the shutdown operation of the sample analyzer 1. When shutting down the sample analyzer 1, the operator issues a shutdown instruction to the information processing unit 5 by selecting the shutdown button (not shown in the drawing) on the screen displayed on the image display 52 via a predetermined operation such as clicking the left mouse button or the like (step S401). When an even of receiving the shutdown instruction is generated, the CPU 51a performs predetermined shutdown operations of the first measuring unit 2 and second measuring unit 3 (step S402). The shutdown operation includes the operation of cleaning the measuring mechanism 2a and the operation of filling sheath fluid in the flow channel within the measuring mechanism 2a. Specifically, the aspirating tube 211 aspirates cleaning agent, for example, CellClean manufactured by Sysmex Corporation, and this aspirated cleaning agent is used to clean the detectors D1 through D3, the flow channels within the measuring mechanism 2a, and the first mixing chamber MC2 and second mixing chamber MC3. The inside of the detectors D1 through D3, the flow channels within the measuring mechanism 2a, and the first mixing chamber MC2 and second mixing chamber MC3 are flushed with the cleaning agent, which is sheath fluid. After flushing with the cleaning agent that is sheath fluid, the flow channels within the measuring mechanism 2 are filled with sheath fluid.

When the shutdown operations of the first measuring unit 2 and second measuring unit 3 are completed, the CPU 51a obtains the current time from the internal clock 51i (step S403), and this time is stored on the hard disk 51d as the shutdown completion time (step S404). Thereafter, the CPU 51a ends the process.

<Start-Up Operation>

In the start-up operation executed when the power supply is turned ON, the sample analyzer of the present embodiment switches to and performs the cleaning operation of the measuring mechanism 2a according to the elapsed time since the 3 completion time of the previous shutdown. This operation is described in detail below.

FIG. 14 is a flow chart showing the flow of the start-up operation of the sample analyzer of the present embodiment. The operator turns ON the power supply of the sample analyzer 1 when using the sample analyzer. After the power supply has been turned ON, the CPU 51a of the information processing unit 5 executes the computer program 54a.

First, the CPU 51a reads the completion time of the previous shutdown from the hard drive 51d (step S301). The CPU 51a then obtains the current time from the internal clock 51i (step S302), and calculates the elapsed time SP from the completion time of the previous shutdown to the current time (step S305).

The CPU 51a then performs the initialization operations of the first measuring unit 2 and second measuring unit 3 (step S304). The initialization operation includes operations for positioning each mechanism part, heating operation of the heater and the like. The CPU 51a then performs first cleaning operations for the first measuring unit 2 and second measuring unit 3 (step S305). The first cleaning operation is not an operation performed in the measurement operation in the measuring mechanism 2a (that is, not a second cleaning operation which will be described later), but does include a flushing operation to eliminate air bubbles within the detectors D1 through D3, and jam elimination operation by applying a pulse voltage to the detectors D1 through D3.

The CPU 51a then determines whether the elapsed time SP is less than 24 hours (step S306). When the elapsed time SP is less than 24 hours (step S306: YES), the CPU 51a sets the parameter RT representing the number of cleanings to [1] (step S307), and the process advances to step S311.

When the elapsed time SP exceeds 24 hours, however, (step S306: NO), the CPU 51a determines whether the elapsed time SP is within five days (step S308). When the elapsed time SP is within five days (step S308: YES), the CPU 51a sets the parameter RT to [3] (step S309), and the process advances to step S311.

When the elapsed time SP exceeds five days (step S308: NO), the CPU 51a sets the parameter RT to [5] (step S310), and the process advances to step S311.

In step S311, the CPU 51a sets the variable i representing of the number of repeated second cleaning operations to [0] (step S311). The CPU 51a then determines whether the variable is less than the number of cleanings RT (step S312); when i is less than the number of cleanings RT (step S312: YES), the second cleaning operation is performed for the first measuring unit 2 and second measuring unit 3 (step S315).

The second cleaning operation is described below. The second cleaning operation is a measurement operation in which a sample is not used. That is, in the second cleaning operation air is suctioned rather than sample by the aspirating tube 211 in the previously mentioned aspirating operation of step S102, and thereafter operations identical to the CBC+DIFF measurement, RBC/PLT measurement, and HGB measurement are performed. In one cycle of the second cleaning operation, a cleaning sequence is performed which includes the CBC+DIFF measurement, RBC/PLT measurement, and HGB measurement without using a sample (hereinafter referred to as "vacant measurement").

In the first measuring unit 2 and second measuring unit 3 of the sample analyzer 1, when air is mixed in, the diluting liquid (sheath fluid) is normally loaded in the flow channels shown in FIGS. 5A and 5B since accurate amounts of sample and reagent are not supplied. This is similar to when the sample analyzer 1 is not started. That is, in the shutdown operation, sheath fluid is loaded in the flow channels of the measuring mechanism 2a, and this condition is maintained until the next start-up. Although sheath fluid is loaded in the flow channels of the measuring mechanism 2a, air bubbles may be generated in the sheath fluid loaded in the flow channels when it has been a long time between the previous shutdown and the power is turned ON the next time. More air bubbles are generated the longer the time between the previous shutdown and the next time the power is turned ON. When air bubbles remain in the flow channel when measuring a sample, the air bubbles become mixed in with the measurement sample or sheath fluid and accurate measurements can not be obtained. Therefore, air bubbles must be eliminated prior to starting the measurement of a sample.

Liquid, such as sheath fluid or the like, is thus removed after a measurement or after cleaning so that the first mixing chamber MC1 and second mixing chamber MC2 are empty. Therefore, when the sample analyzer 1 has stopped after the shutdown operation, the first mixing chamber MC1 and second mixing chamber MC2 are empty. Although the inner surfaces of the first mixing chamber MC1 and second mixing chamber MC2 are coated with adhered or leaked sheath fluid immediately after the shutdown operation, the inner surfaces of the first mixing chamber MC1 and second mixing chamber MC2 become dry and the components of the sheath fluid crystallize on and soil these inner surfaces when the first mixing chamber MC1 and second mixing chamber MC2 are not used for a long time. This soiling adversely affects measurement precision. Therefore, before starting a sample measurement, the inner surfaces of the first mixing chamber MC1 and second mixing chamber MC2 must be adequately wetted.

The previously mentioned vacant measurement is performed to eliminate this soiling and air bubbles, and ensure the wetness of the parts used in measurements. That is, by performing a cleaning operation which is similar to the measurement operation, the flow channels used in measurements in the measuring mechanism 2a can be cleaned, the soiling and air bubbles can be removed from the flow channels, and the flow channels can be sufficiently wetted.

After the vacant measurement is performed, the CPU 51a increments the variable i by [1] (step S314), and subsequently returns to the process of step S312. Thus, the number of repetitions of the cleaning sequence changes according to the length of the elapsed time SP. That is, the vacant measurement is performed once when the elapsed time SP is less than 24 hours, the vacant measurement is performed 3 times when the elapsed time SP s greater than 24 hours but less than 5 days, and the vacant measurement is performed 5 times when the elapsed time SP is greater than 5 days. When the elapsed time SP is long, are large amount of air bubbles generated in the flow channel can be eliminated by repeating the vacant measurement (cleaning sequence) numerous times. When the elapsed time is short, the time of the cleaning operation can be curtailed since fewer air bubbles are generated.

Returning now to FIG. 14, when the variable i is less than the number of cleanings RT in step S312 (step S312: NO), the CPU 51a performs a blank check operation (step S315). The blank check operation is identical to the previously described vacant operation, that is, the CPU 51a executes a measurement operations without a sample in the first measuring unit 2 and second measuring unit 3 and analyzes the obtained measurement data, and obtains the analysis results of each measurement item of the RBC, PLT, HGB, NEUT, LYMPH, EO, BASO, MONO, and WBC. The CPU 51a determines whether the analysis result obtained by the blank check operation is less than a predetermined standard value (step S316), and displays an anomaly warning screen (not shown in the drawing), indicating that the sample analyzer 1 may be in an abnormal condition, on the image display 52 (step S317) when the analysis result of a measurement item exceeds the standard value (step S316: NO), whereupon the process ends. However, when the analysis result of the blank check of all measurement items is less than the standard value (step S316: YES), the CPU 51a moves the states of the first measuring unit 2 and second measuring unit 3 to a measurement standby state (step S318), whereupon the process ends.

According to this construction, a suitable cleaning operation can be performed according to the time elapsed since the previous shutdown. The adverse affect of air bubbles and adhered soiling on measurement precision can be suppressed by adequately cleaning when it has been a long time since the previous shutdown. The waiting time to perform a sample measurement can be reduced by a simple cleaning when it has been a short time since the previous shutdown.

Furthermore, a plurality of separate control programs for performing pluralities of cleaning operations are not required to increase the number of times the vacant measurement cleaning sequence is performed in accordance with the increase in the time elapsed since the previous shutdown. Therefore, control of the measuring units can be realized to increase the time of the cleaning operation according to the length of the elapsed time while reducing the burden on the program clock. Since the cleaning sequence is a vacant measurement, the flow channel used for measuring a sample can be accurately cleaned in direct relation to measurement precision.

Although the sheath fluid reagent is consumed in the vacant measurement, the amount of consumed reagent is reduced by decreasing the number of vacant measurements when the elapsed time since the previous shutdown is short.

Other Embodiments

Note that although the sample analyzer 1 of the present embodiment is a multifunction analyzer, the present invention is not limited to this arrangement inasmuch as the present invention may be adapted to various sample processing apparatuses. For example, in other sample analyzers such as blood coagulation measuring apparatuses, immunoanalyzers, biochemical analyzers, urine analyzers, or blood smear sample preparing apparatuses, the cleaning operation in the start-up operation can be changed according to the elapsed time since the cleaning operation in the previous shutdown operation.

Although the above embodiment has been described in terms of changing the cleaning operation according to the elapsed time since the completion of the previous shutdown, the present invention is not limited to this arrangement. The cleaning operation may also be changed according to the elapsed time since the previous start-up began. The cleaning operation may also be changed according to the elapsed time since the start or end of the previous cleaning operation. In this case, the next cleaning operation can be changed according to elapsed time since the previous cleaning operation when the measuring unit is starting up, the measuring unit is in a working state or idle state when there is no elapsed time since the cleaning operation in the shutdown operation.

Although the above embodiment has been described in terms of changing the number of repetitions of the cleaning sequence according to the elapsed time since the completion of the previous shutdown, the present invention is not limited to this arrangement. For example, the part for cleaning within the measuring mechanism 2a according to the elapsed time from the completion of the previous shutdown can be changed so that all flow channels used in the CBC+DIFF measurement, RBC/PLT measurement, and HGB measurement are cleaned when the elapsed time from the completion of the previous shutdown is longer than a predetermined time; and only the flow channels used in the CBC+DIFF measurement and RBC/PLT measurement are cleaned and the flow channels used in the HGB measurement are not cleaned when the elapsed time since the previous shutdown is shorter than the predetermined time. As a further example, the content of the cleaning operation according to the elapsed time from the completion of the previous shutdown can be changed so that the first cleaning operation and second cleaning operation are both performed when the elapsed time since the completion of the previous shutdown is longer than a predetermined time, and only the second cleaning operation is performed when the elapsed time since the completion of the previous shutdown is shorter than the predetermined time. The cleaning agent may also be changed to a stronger cleaning agent when the elapsed time since the completion of the previous shutdown is longer than a predetermined time. The flow speed of the sheath fluid used when cleaning the flow channels may also be reduced when the elapsed time since the completion of the previous shutdown is longer than a predetermined time.

Although the above embodiment has been described in terms of performing different cleaning operations at start-up and shutdown, the content of the cleaning operation is not limited insofar as the common parts are cleaned by cleaning operation performed during the shutdown operation and the cleaning operation performed during the start-up operation. For example, the cleaning operation may be common to the cleaning operation performed during the shutdown operation and the cleaning operation performed during the start-up operation.

Although the above embodiment has been described in terms of a sample analyzer 1 provided with a first measuring unit 2 and a second measuring unit 3, the present invention is not limited to this arrangement. The sample analyzer may also be configured by a single measuring unit and a single information processing unit. The measuring unit and information processing unit need not be provided separately, inasmuch as the sample analyzer may be provided with a single housing which incorporates the functions of the measuring unit and the functions of the information processing unit.

Although the above embodiment has been described in terms of a first measuring unit 2 and second measuring unit 3 that are not provided with an operation unit such as a CPU or the like, wherein the operational control of the first measuring unit 2 and second measuring unit 3 is accomplished by the CPU 51a of the information processing unit 5, the present invention is not limited to this arrangement. The measuring unit may also be provided with a controller configured by a CPU, memory and the like, so that operational control of the measuring mechanism is performed by this controller.

Although the above embodiment has been described in terms of performing all processes of the computer program 54a via a single computer, the present invention is not limited to this arrangement inasmuch as the same processes of the computer program 54a can be distributed to a plurality of devices (computers) in a distributed system.

What is claimed is:
1. A sample processing apparatus, comprising:
a sample processing mechanism which comprises
   a mixing chamber configured to be used for processing a measurement sample from a reagent and a sample which is a blood or a urine,
   a detector configured to measure the measurement sample, and
   a flow channel configured to supply the measurement sample to the detector from the mixing chamber, and
   wherein the sample processing mechanism performs a sample processing operation for preparing the measurement sample and measuring the measurement sample; and
a processor and a memory storing a computer program that enables the processor to:
   control the sample processing mechanism to perform the sample processing operation and obtain a detection result of the measurement sample,
   control the sample processing mechanism to perform a shutdown cleaning operation by using a cleaning agent in a shutdown operation of the sample processing apparatus, wherein the cleaning agent does not include the reagent; and
   control the sample processing mechanism to perform a cleaning operation sequence for cleaning the mixing chamber, the detector and the flow channel when the sample processing mechanism performs a start-up operation, the cleaning operation sequence comprising a vacant measurement operation performed by using the reagent and suctioned air rather than the sample, the vacant measurement operation is changed depending on a time elapsed since the shutdown operation, and a blank measurement operation performed without using the sample,
   wherein the computer program enables the processor to control the sample processing mechanism to perform the vacant measurement operation for a longer time as the elapsed time is longer, and
   the sample processing mechanism is configured to prepare a measurement sample from the sample and the reagent in the sample processing operation, prepare a vacant measurement sample, prepare a blank measurement sample without the sample using the reagent in the blank measurement operation,
   the processor is programmed to:
   control the sample processing mechanism to perform the vacant measurement operation and not to obtain a detection result of the vacant measurement sample, and
   control the sample processing mechanism to perform the blank measurement operation and obtain a detection result of the blank measurement sample.
2. The sample processing apparatus of claim 1, wherein
the sample processing mechanism is configured to perform the vacant measurement operation, once or several times, for cleaning the mixing chamber, the detector and the flow channel by a predetermined procedure; and
the computer program enables the processor to control the sample processing mechanism to perform the vacant measurement operation more times as the elapsed time is longer.
3. The sample processing apparatus of claim 2, wherein the computer program enables the processor to determine a number of executions of the vacant measurement operation based on the elapsed time, and control the sample processing mechanism to perform the determined number of executions.

4. The sample processing apparatus of claim 3, wherein the computer program enables the processor to determine the number of executions of the vacant measurement operation as a first number of times when the elapsed time has not exceeded a threshold time, and determine the number of executions of the vacant measurement operation as a second number of times greater than the first number of times when the elapsed time has exceeded the threshold time.

5. The sample processing apparatus of claim 4, wherein the computer program enables the processor to determine the number of executions of the vacant measurement operation as a third number of times greater than the second number of times when the elapsed time has exceeded a second threshold time which is longer than the threshold time.

6. The sample processing apparatus of claim 2, wherein the sample processing mechanism further comprises:
   an aspirator configured to aspire the sample, and
   a reagent supplier configured to supply the reagent to be used for processing the sample,
   wherein the detector is configured to detect characteristic information representing characteristics of the sample; and
   the computer program enables the processor to control the sample processing mechanism to perform the vacant measurement operation comprising an operation of supplying the reagent supplied from the reagent supplier through the flow channel to the detector from the mixing chamber without aspirating the sample by the aspirator.

7. The sample processing apparatus of claim 6, wherein
   the detector performs, in the blank measurement operation, a detection operation on the reagent supplied from the reagent supplier, the detection operation being identical to an operation of detecting the characteristic information of the sample; and
   the computer program enables the processor to determine a condition of the sample processing apparatus, based on the detection result obtained by performing the detection operation on the reagent.

8. The sample processing apparatus of claim 1, wherein the reagent is a dilution liquid, and
   the computer program enables the processor to control the sample processing mechanism to prepare the measurement sample from the sample and the dilution liquid, and clean the mixing chamber, the detector and the flow channel in the vacant measurement operation using the dilution liquid.

9. The sample processing apparatus of claim 1, further comprising a time outputter configured to output a current time,
   wherein the computer program enables the processor to obtain the elapsed time based on the time output by the time outputter, and control the vacant measurement operation by the sample processing mechanism based on the obtained elapsed time.

10. The sample processing apparatus of claim 1, wherein the shutdown cleaning operation performed in a current shutdown operation is different from the vacant measurement operation performed after a previous shutdown operation.

11. The sample processing apparatus of claim 1 which functions as one of a blood cell analyzer configured to test the blood and a urine analyzer configured to test the urine.

12. A sample processing apparatus comprising:
   a sample processing mechanism which comprises
      a mixing chamber configured to prepare a measurement sample from a first reagent, a second reagent and a blood sample,
      a hemolytic agent supplier configured to supply a hemolytic agent as the first reagent to the mixing chamber,
      a stain liquid supplier configured to supply a stain liquid as the second reagent to the mixing chamber,
      a detector configured to measure the measurement sample and
      a flow channel configured to supply the measurement sample to the detector from the mixing chamber, and performs a sample processing operation for preparing the measurement sample and measuring the measurement sample; and
   a processor and a memory storing a computer program that enables the processor to:
      control the sample processing mechanism to perform the sample processing operation and obtain a detection result of the measurement sample,
      control the sample processing mechanism to perform a shutdown cleaning operation in a shutdown operation of the sample processing apparatus; and
      control the sample processing mechanism to perform a cleaning operation sequence for cleaning the mixing chamber, the detector and the flow channel when the sample processing mechanism performs a start-up operation, the cleaning operation sequence comprising a vacant measurement operation performed by using the first and second reagents and suctioned air rather than the sample, the vacant measurement operation is changed depending on a time elapsed since the shutdown operation, and a blank measurement operation performed by using the first and second reagents without using the sample,
   wherein the sample processing mechanism performs the shutdown cleaning operation by using a cleaning agent, wherein the cleaning agent does not include the first or second reagents,
   prepares a vacant measurement sample without the blood sample using the first and second reagents,
   prepares a blank measurement sample without the blood sample using the first and second reagents, and
   the processor is programmed to:
      control the sample processing mechanism to perform the vacant measurement operation and not to obtain a detection result of the vacant measurement sample, and
      control the sample processing mechanism to perform the blank measurement operation and obtain a detection result of the blank measurement sample.

13. The sample processing apparatus of claim 12, wherein the computer program enables the processor to control the sample processing mechanism to perform the vacant measurement operation for a longer time as the elapsed time is longer.

14. The sample processing apparatus of claim 12, wherein the sample processing mechanism is configured to perform the vacant measurement operation, once or several times, for cleaning the flow channel by a predetermined procedure; and
   the computer program enables the processor to control the sample processing mechanism to perform the vacant measurement operation more times as the elapsed time is longer.

15. The sample processing apparatus of claim 14, wherein the computer program enables the processor to determine a number of executions of the vacant measurement operation based on the elapsed time, and control the sample processing mechanism to perform the determined number of executions.

16. The sample processing apparatus of claim 15, wherein the computer program enables the processor to determine the number of executions of the vacant measurement operation as a first number of times when the elapsed time has not exceeded a threshold time, and determine the number of executions of the vacant measurement operation as a second number of times greater than the first number of times when the elapsed time has exceeded the threshold time.

17. The sample processing apparatus of claim 14, wherein the sample processing mechanism further comprises:
   an aspirator configured to aspire the blood sample;
   a dilution liquid supplier configured to supply the dilution liquid to be used for diluting the blood sample;
   a second mix chamber for preparing a second measurement sample from the blood sample and the dilution liquid;
   a second detector configured to detect characteristic information representing characteristics of the second measurement sample, and
   a second flow channel configured to supply the second measurement sample to the second detector from the second mixing chamber,
   wherein the detector configured to detect characteristic information representing characteristics of the measurement sample,
   wherein the computer program enables the processor to control the sample processing mechanism to perform the vacant measurement operation comprising an operation of preparing a second vacant measurement sample using the dilution liquid supplied from the dilution liquid supplier without using the blood sample and an operation of supplying the second vacant measurement sample to the second detector from the second mixing chamber via the second flow channel.

18. The sample processing apparatus of claim 17, wherein the second detector performs, in the blank measurement operation, a detection operation on a second blank measurement sample prepared by using the dilution liquid supplied from the dilution liquid supplier, the detection operation being identical to an operation of detecting the characteristic information of the second measurement sample; and
   the computer program enables the processor to determine a condition of the sample processing apparatus, based on a detection result obtained by performing the detection operation.

19. The sample processing apparatus of claim 12, which functions as a blood cell analyzer configured to test the blood sample.

* * * * *